(12) United States Patent
Wright

(10) Patent No.: US 11,680,874 B2
(45) Date of Patent: Jun. 20, 2023

(54) DEVICE, SYSTEM AND METHOD FOR CORRELATING CORE SAMPLE ZONES WITH ACTUAL SUBTERRANEAN DEPTH

(71) Applicant: COASTLINE TECHNOLOGIES INC., Cobble Hill (CA)

(72) Inventor: Tom A Wright, Cobble Hill (CA)

(73) Assignee: COASTLINE TECHNOLOGIES INC., Cobble Hill (CA)

( * ) Notice: Subject to any disclaimer, the term of this patent is extended or adjusted under 35 U.S.C. 154(b) by 224 days.

(21) Appl. No.: 17/331,819

(22) Filed: May 27, 2021

(65) Prior Publication Data

US 2021/0285850 A1   Sep. 16, 2021

Related U.S. Application Data

(62) Division of application No. 16/486,992, filed as application No. PCT/CA2018/050236 on Mar. 1, 2018, now Pat. No. 11,047,771.

(51) Int. Cl.
| | |
|---|---|
| *G01N 1/08* | (2006.01) |
| *E21B 25/00* | (2006.01) |
| *E21B 47/04* | (2012.01) |
| *G01D 5/165* | (2006.01) |
| *G01N 33/24* | (2006.01) |
| *E02F 5/00* | (2006.01) |

(52) U.S. Cl.
CPC .............. *G01N 1/08* (2013.01); *E21B 25/00* (2013.01); *E21B 47/04* (2013.01); *G01D 5/165* (2013.01); *G01N 33/24* (2013.01); *E02F 5/006* (2013.01)

(58) Field of Classification Search
CPC .......... G01N 1/08; G01N 33/24; E21B 25/00; E21B 47/04; G01D 5/165; E02F 5/006
See application file for complete search history.

(56) References Cited

U.S. PATENT DOCUMENTS

| | | |
|---|---|---|
| 4,735,269 A | 4/1988 | Park et al. |
| 5,537,753 A | 7/1996 | Otte et al. |
| 5,553,677 A | 9/1996 | Hinz |

(Continued)

FOREIGN PATENT DOCUMENTS

WO     2010148435     12/2010

OTHER PUBLICATIONS

Examination Notes for International Patent Application PCT/CA2018/050236 dated Nov. 15, 2018 (2 pages).

(Continued)

*Primary Examiner* — Dany E Akakpo
(74) *Attorney, Agent, or Firm* — Sand, Sebolt & Wernow Co., LPA

(57) ABSTRACT

Disclosed herein is a device and method for correlating core sample zones with an actual subterranean depth. The disclosed device has a pair of independent distance measuring devices operably in communication with a core sample apparatus where a first distance measuring device measures the length of a core sample entering a core sampling tube and a second distance measuring device measures a drive depth of the core sampling tube entering into the ground. A processing unit is provided for correlating the two distances so as to allow a determination as to the actual depth below ground from where a given zone of the core sample is extracted.

10 Claims, 8 Drawing Sheets

(56) References Cited

U.S. PATENT DOCUMENTS

| | | | |
|---|---|---|---|
| 6,457,538 B1* | 10/2002 | Pittard | E21B 47/20 |
| | | | 175/46 |
| 7,784,564 B2 | 8/2010 | Iskander et al. | |
| 8,550,184 B2 | 10/2013 | Buchanan et al. | |
| 8,960,327 B2 | 2/2015 | Stockton | |
| 2007/0061079 A1* | 3/2007 | Hu | E21B 25/00 |
| | | | 702/6 |
| 2014/0182935 A1 | 7/2014 | Weaver et al. | |

OTHER PUBLICATIONS

International Search Report of the ISA for International Patent Application PCT/CA2018/050236 dated Nov. 15, 2018 (5 pages).

Non-Final Office Action for U.S. Appl. No. 16/486,992, dated Oct. 29, 2020 (16 Pages).

Written Opinion of the ISA for International Patent Application PCT/CA2018/050236 dated Nov. 15, 2018 (6 pages).

* cited by examiner

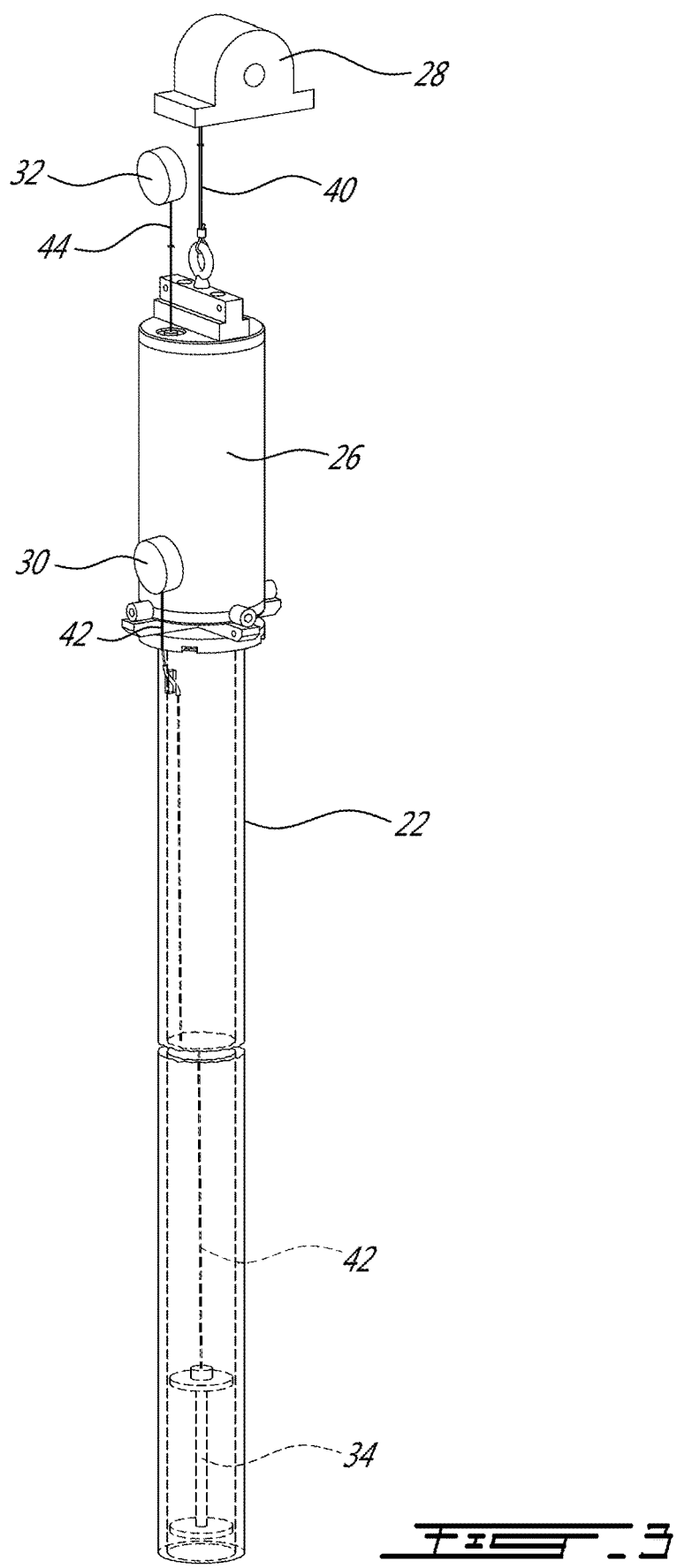

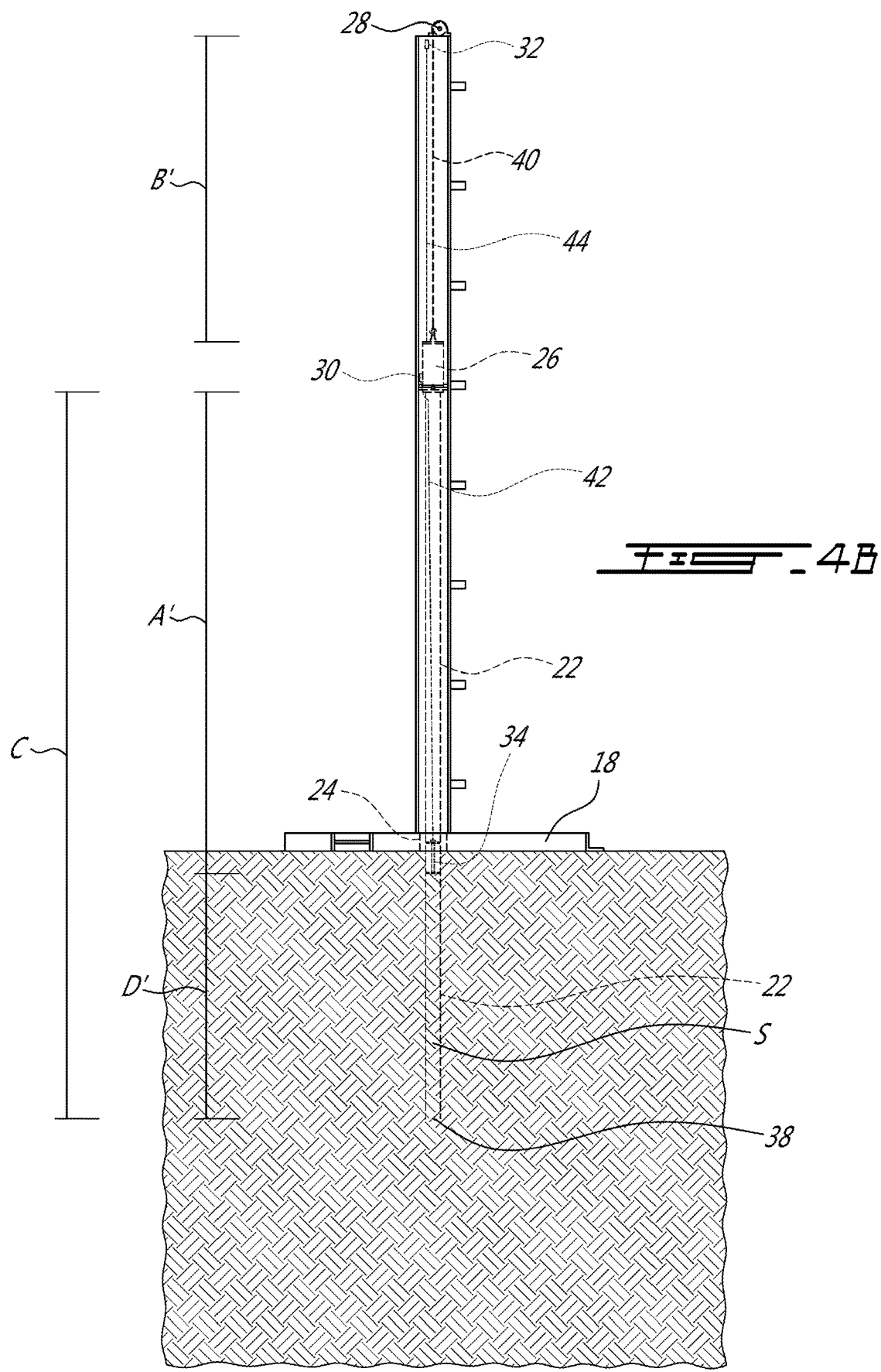

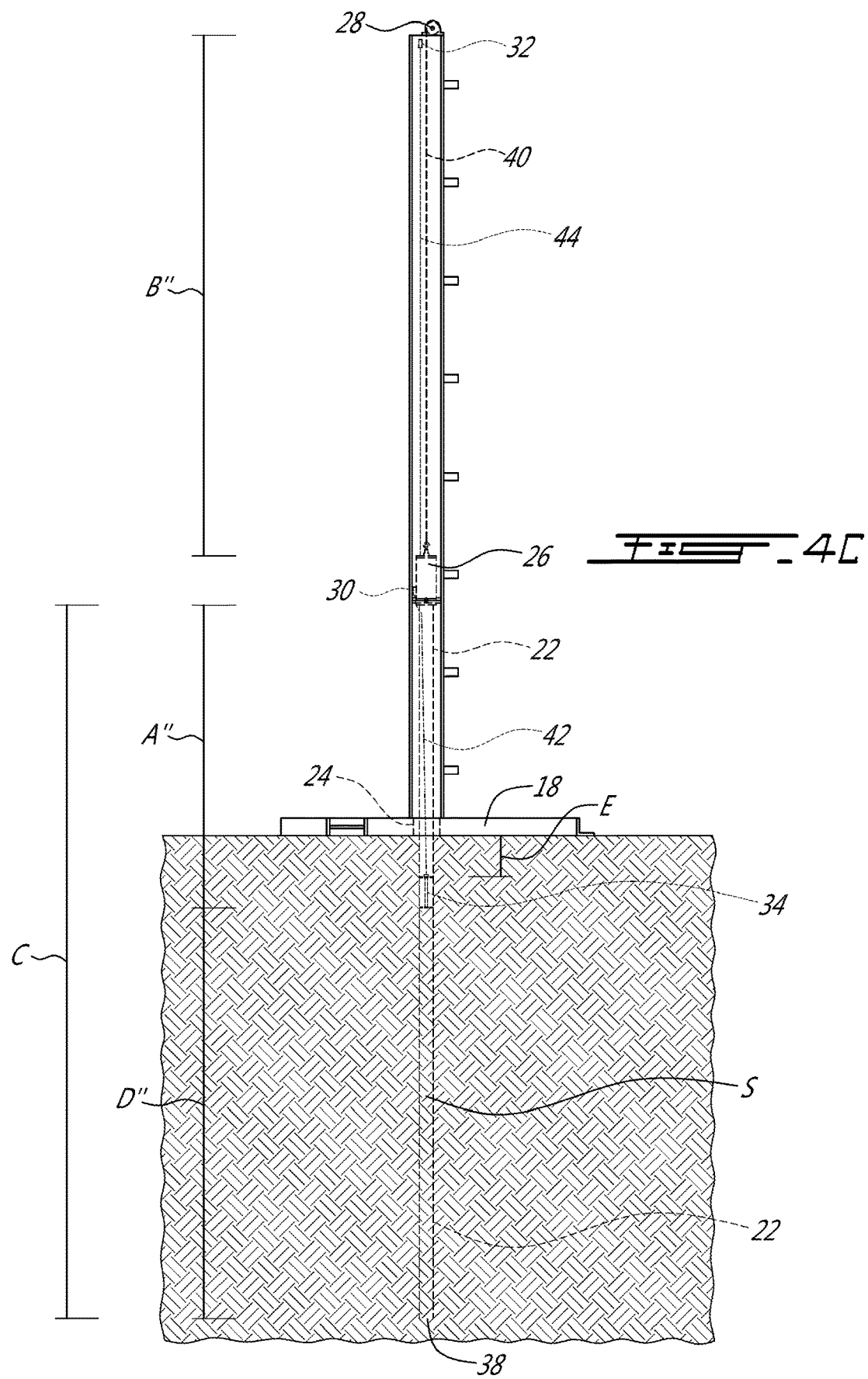

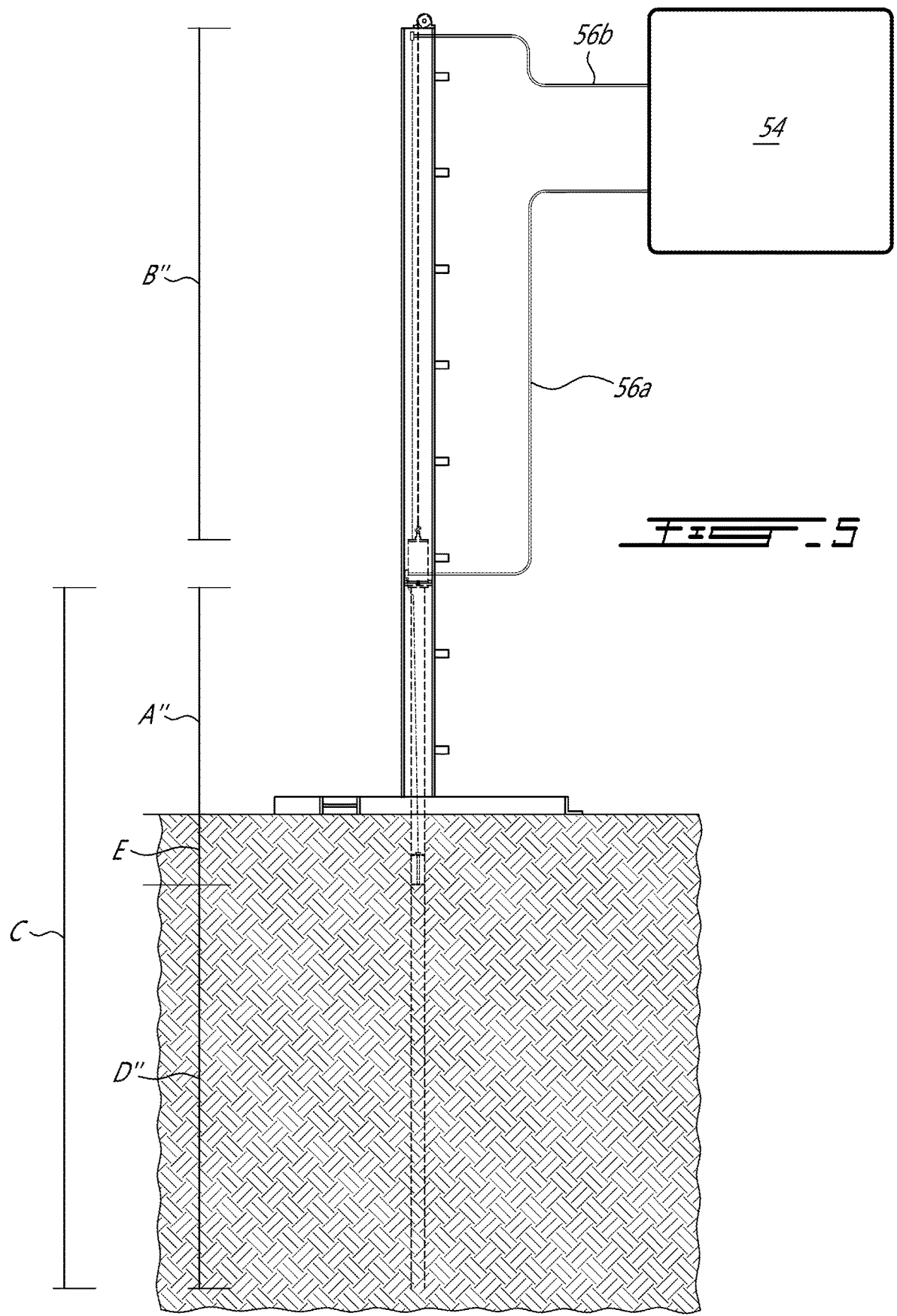

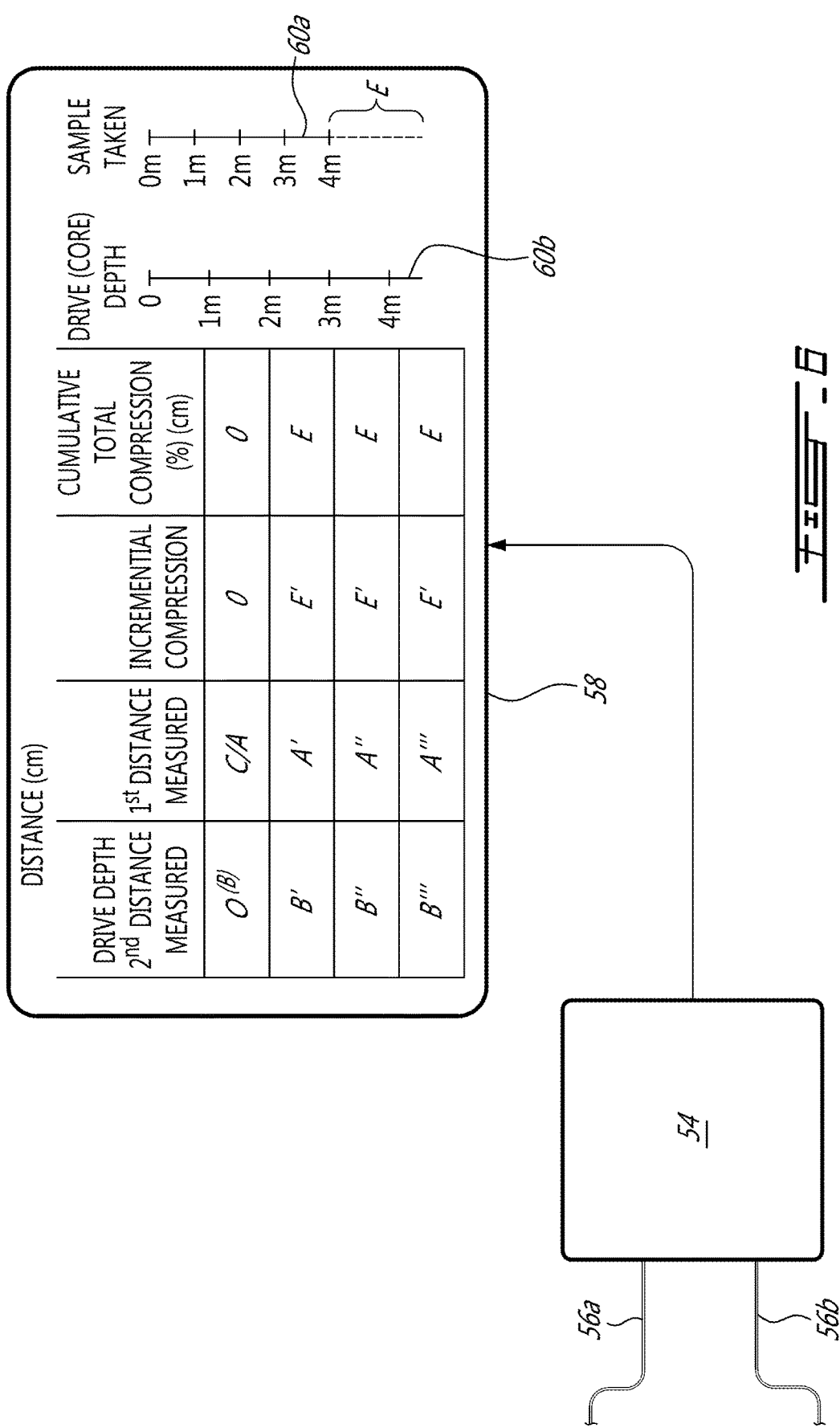

DEVICE, SYSTEM AND METHOD FOR CORRELATING CORE SAMPLE ZONES WITH ACTUAL SUBTERRANEAN DEPTH

RELATED APPLICATIONS

The present application is a Divisional Application of U.S. patent application Ser. No. 16/486,992, filed Aug. 19, 2019, which in turn is the United States National Phase Entry of International Patent Application serial number PCT/CA2018/050236, filed Mar. 1, 2018, which claims benefit of priority to Canadian Patent Application serial number 2,959,911 entitled "DEVICE, SYSTEM AND METHOD FOR CORRELATING CORE SAMPLE ZONES WITH ACTUAL SUBTERRANEAN DEPTH" filed Mar. 6, 2017, the disclosures of which is herein incorporated by reference.

TECHNICAL FIELD

The present disclosure relates to a core sample measuring device and system for correlating one or more zones in a core sample with an actual subterranean depth.

BACKGROUND

Core sampling is a technique that is often employed in order to gain an understanding of the composition of various subterranean sediment layers. Additionally, core sampling can be useful in order to determine if contaminants are present within the various layers. In certain applications core sampling can be used to locate a subterranean depth where various sediment layers such as silt, sand, cobble, dirt, etc. are found. After recovery, a core sample then can be analyzed for sediment types and pollutants. Such information can be useful for future dredging operations, among other types of operations, to provide information to technicians or operators as to where a layer and/or possible pollutants can be found below the earth's surface. Therefore, during subsequent dredging operations, technicians know approximate depths to dig to in order to remove a desired layer or pollutant zone.

Dredging, treatment and disposal of sediment layers is very expensive. Accordingly, it is useful for dredging technicians to have information about the depths to which they must dredge in order to recover the desired subterranean sediment zones or layers. Dredging too deep will increase dredging and treatment costs. Dredging too shallow may not recover the desired subterranean sediment layers, which may result in pollutants not being recovered and sediment layers not being adequately treated, removed and/or remediated.

For example, the disposal of marine sediments from dredging often requires studies to confirm pollutant levels and the depth where such pollutants can be found for disposal and/or remediation. Core sampling can be used to provide information regarding the type and subterranean depths of such pollutants in addition to the sediment types. Briefly, in order obtain a core sample, a sampler, often a core sampling tube, is driven into the ground, which may be underwater, thus penetrating the sediment layers. Some of the sediment enters into the core sampling tube and is retained therein and when the core sampler tube is extracted from the ground or sea bottom, the core sample can be analyzed.

The core sampling tube may be driven into the ground by weighted and rotational forces, brute force such as a hammering, or in many preferred modern applications by weighted and vibrational forces. In the case of weighted and vibrational forces, vibrational energy is applied to the core sampling tube as it is allowed to enter the ground or seabed as a downward force is applied either under gravity or a net applied downward force. The application of the vibrational energy to the core sampling tube, known as vibracoring, and the resulting vibratory displacement causes a partial fluidization of the sediment in direct contact with the core sampling tube and thus the friction between the core sampling tube and the sediment is reduced. The core sampling tube can then penetrate the ground to a desired depth. Once the desired depth is reached, the core sampling tube is extracted and the core sample therein can be analyzed.

Although vibracoring is a preferred process for obtaining core samples, as well as other forms of core sampling, there are certain drawbacks. For example, during the core sampling process an operator does not know whether sediment is entering the core sampling tube as it enters the ground. Accordingly, if the core sample taken is not adequate, the process must be repeated which consumes time and ultimately will affect scheduling. An experienced operator will have a sense as to whether a given coring process is going well and if the operator does not sense that the coring is going well, they can abort and restart the process. Yet, this relies heavily on experience and is not an exact science. However, with current vibracoring technologies there is no certain way for an operator to know if a sample is entering into the core sampling tube, as required, let alone if the core sample is adequate. Furthermore, as a core sample enters the core sampling tube it may be compressed in certain zones based on the sediment layers through which the core sampling tube has penetrated. Therefore, when the core sample is extracted for analysis the revealed subterranean depth of the various core sample zones in the core sample may not correspond to the true subterranean depth from which it was taken.

It would be useful to develop a device and system where an operator will know whether a core sample is entering the core sampling tube and also to be able to know the true subterranean depth from where a particular core sample zone has been taken.

This background information is provided to reveal information believed by the applicant to be of possible relevance. No admission is necessarily intended, nor should it be construed, that any of the preceding information constitutes prior art.

SUMMARY

The following presents a simplified summary of the general inventive concepts described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

In one aspect, there is provided a device for correlating core sample zones with an actual subterranean depth. The device comprises a rig frame having a rig foot, with a rig foot aperture, operably coupled to a rig lower end thereof and a component mounting surface coupled near a rig upper end thereof. A core sampling tube and motor for imparting forces on the core sampling tube are provided and located within the rig frame. The core sampling tube is dependable through the rig foot aperture via a core sampling tube lowerer operable with the component mounting surface for lowering the core sampling tube downward so as to depend through the rig foot aperture. Additionally, there is provided a first distance measuring device in communication with a core sampler puck where the core sampler puck is maintained within and movable along an internal length of said core sampling tube and a second distance measuring device in communication with an external point located near an upper end of the core sampling tube. The first distance measuring device is provided for measuring a decreasing distance between the core sampler puck and the upper end of the core sampling tube and the second distance measuring device is provided for measuring an increasing distance between the upper end of the core sampling tube and the component mounting surface as the core sampling tube is depended through the rig foot aperture into the ground and a core sample enters the core sampling tube. The decreasing distance and the increasing distance are thus correlatable so as to render the actual subterranean depth corresponding to a given zone within said core sample.

In some embodiments of the device, the device is adapted to be mountable to a boat, a crane, a barge, a truck, a tracked-vehicle or a static structure.

In some embodiments of the device, a lower end of the core sampling tube has a cutter tip integrally formed thereon or operably coupled thereto.

In some embodiments of the device, the motor is provided as a vibratory motor for imparting vibratory forces on the core sampling tube. In some other embodiments, the motor is provided as a rotational motor for imparting rotational forces on the core sampling tube so as to cause rotation of said core sampling tube.

In some embodiments of the device, the core sampling tube lowerer is a winch having a winch line operably coupled near the upper end where the winch line is extendable and retractable so as to allow the core sampling tube to extend and retract though the rig foot aperture.

In some embodiments of the device, the first distance measuring device and/or the second distance measuring device is provided as a laser measuring device, a radio frequency measuring device, an infrared measuring device or a string potentiometer line measuring device. In preferred embodiments, the first and second distance measuring devices are provided as string potentiometer line measuring devices.

In preferred embodiments, the motor is provided as a vibratory motor and is operably coupled to the upper end of said core sampling tube.

In preferred embodiments, the first distance measuring device is provided as a first string potentiometer located near the upper end and is movable in unison with the core sampling tube where the first string potentiometer has a first string potentiometer line coupled at an end thereof to the core sampler puck. Furthermore, in some preferred embodiments, the first string potentiometer is mounted externally on the vibratory motor and the first string potentiometer line depends through a core sampling tube aperture such that the first string potentiometer line can extend and retract as the core sampler puck moves along the internal length of the core sampling tube. In some embodiments, the device further comprises a line guide for guiding the first string potentiometer line through the core sampling tube aperture. Additionally, in some embodiments, the second distance measuring device is provided as a second string potentiometer statically located near the component mounting surface and having a second string potentiometer line coupled at an end thereof to near the upper end of the core sampling tube.

In preferred embodiments, the second string potentiometer is statically located on the component mounting surface and has a second string potentiometer line coupled to an external point being located on the motor.

In preferred embodiments, the core sampling tube lowerer is, as noted above, provided as a winch where the winch is mounted to the component mounting surface and having a winch line operably coupled to said vibratory motor, said winch line being extendable and retractable so as to allow the core sampling tube to extend and retract though the rig foot aperture.

In another aspect of the device, the first distance measuring device and the second distance measuring device are each capable of outputting electronic signals. In such embodiments, the electronic signals corresponding to:

for the first distance measuring device, the distance between said core sampler puck and said upper end; and for the second distance measuring device, the upper end and the component mounting surface.

In some embodiments, the device further comprises a processing unit for receiving and processing the electronic signals from the first distance measuring device and the second distance measuring device where the processing unit is capable of outputting indicia of the actual subterranean depths and corresponding core sample zones.

In yet another aspect, there is provided a non-transitory computer-readable medium comprising statements and instructions for implementation by a computer system in correlating the electronic signals outputted from the first and second distance measuring devices so as to render the actual subterranean depth corresponding to a given zone within said core sample.

In some embodiments, the transitory computer-readable medium is further configured to provide a chart to a user of the actual subterranean depth corresponding to a given zone within said core sample. Additionally, in some embodiments, the transitory computer-readable medium is further configured to provide a graphical representation to a user of the actual subterranean depth corresponding to a given zone within said core sample.

In yet another aspect, there is provided a method for correlating core sample zones with an actual subterranean depth. The method comprising:

providing a rig frame having a rig foot, with a rig foot aperture, operably coupled to a rig lower end thereof and a component mounting surface coupled near a rig upper end thereof;

providing a core sampling tube and motor for imparting forces on said core sampling tube located within the rig frame, said core sampling tube being dependable through the rig foot aperture;

providing a first distance measuring device in communication with a core sampler puck, the core sampler puck being maintained within and movable along an internal length of the core sampling tube, the first distance measuring device for measuring a decreasing distance between the core sampler puck and the upper end as the core sampling tube is depended through the rig foot aperture into the ground and a core sample enters the core sampling tube;

providing a second distance measuring device in communication with an external point located near an upper end of the core sampling tube, the second distance measuring device for measuring an increasing distance between the upper end and the component mounting surface as the core sampling tube is depended through the rig foot aperture into the ground and a core sample enters the core sampling tube;

lowering the core sampling tube through said rig foot aperture; and correlating said decreasing distance and said increasing distance so as to render the actual subterranean distance corresponding to a given zone within said core sample.

In some embodiments of the method, the first distance measuring device and the second distance measuring device are each capable of outputting electronic signals corresponding to:

for the first distance measuring device, the distance between the core sampler puck and the upper end; and for the second distance measuring device, the upper end and the component mounting surface.

In some embodiments, the method further comprises forwarding the electronic signals to a processing unit capable of receiving and processing the electronic signals from the first distance measuring device and the second distance measuring device; and the processing unit outputting indicia of the actual subterranean depths and corresponding core sample zones.

In other words, in preferred embodiments the instantly disclosed device and system employs a mechanical system with two string potentiometers. The first string potentiometer has a line connected to an internal core sampler puck designed to reside inside the core sampling tube at the sediment/ground or sediment/water interface before the coring process has begun and movable along the core sampling tube length during coring. A second string potentiometer having a line connected to a portion of an upper end of the core sampling tube is provided for measuring the external depth of penetration of the core sampling tube. A first potentiometer spool of the first string potentiometer and a second potentiometer spool of the second string potentiometer are both equipped with electronics and electronic instructions to measure the rotation of the spools and translate this rotation into distance measurement. Based on a differential measurement between the first string potentiometer spool and the second string potentiometer spool, the electronic instruction are executable to provide the operator with information showing the comparison of external penetration measurement (drive depth) versus the measurement of a core sample or sediment length entering the core. Furthermore, based on the differential measurements, a given zone a core sample can be correlated with an actual depth corresponding to the given subterranean zone.

Technologies such as lasers, optical distance and radio frequency measurement instruments are limited in their application for subsea environment since measurements are made inside the core sampling tube during coring in order to determine if a sample is entering the core sampling tube. The use of lasers, optical distance and radio frequency measuring devices is hindered in subsea applications due to interference with lasers, optical distance and radio frequency measurement systems as a result of the turbidity at the sediment/water interface (bottom of the core sampling tube) as well as reflective interference owing the core sampling tube length and medium density. Additionally, vibrations associated with vibracoring processes may interfere with the optical measuring components mounted at or on the core sampling tube/powerhead interface systems. However, such distance measuring devices may be employable in terrestrial based applications.

In one aspect there is provided a non-transitory computer-readable medium comprising computer-executable instructions for correlating core sample zones in a core sample taken using a core sampling tube, with an actual subterranean depth, by: measuring, via a first measuring device, a decreasing distance between a core sampler puck maintained within and movable along an internal length of the core sampling tube, and an upper end of the core sampling tube and measuring, via a second measuring device, an increasing distance to an upper end of the core sampling tube as the core sampling tube is passed into the ground and the core sample enters the core sampling tube. The decreasing distance and the increasing distance are correlated so as to render the actual subterranean depth corresponding to a given core sample zone within the core sample.

In some embodiments, the non-transitory computer-readable medium further comprises instructions to output a chart rendering the actual subterranean depth corresponding to the given zone within the core sample.

In some embodiments, the non-transitory computer-readable medium further comprises instructions to output a graphical representation of the actual subterranean depth corresponding to the given zone within the core sample.

In some embodiments, the non-transitory computer-readable medium further comprises instructions to output indicia of the actual subterranean depths corresponding to respective zones within the core sample.

In some embodiments, the correlating accounts for a compaction of the core sample tube as the core sampling tube is passed into the ground and the core sample enters the core sampling tube.

In yet another aspect, there is provided a computer-implemented method, to be implemented by a processing unit, for correlating core sample zones in a core sample taken using a core sampling tube, with an actual subterranean depth, comprising:

measuring, via a first measuring device, a decreasing distance between a core sampler puck maintained within and movable along an internal length of the core sampling tube, and an upper end of the core sampling tube;

measuring, via a second measuring device, an increasing distance to an upper end of the core sampling tube as the core sampling tube is passed into the ground and the core sample enters the core sampling tube; and correlating said decreasing distance and said increasing distance so as to render the actual subterranean depth corresponding to a given core sample zone within the core sample.

In some embodiments of the computer-implemented method, the method further comprises rendering the actual subterranean depth corresponding to said given zone within the core sample in a chart.

In some embodiments of the computer-implemented method, the method further comprises outputting a graphical representation of the actual subterranean depth corresponding to said given zone within the core sample.

In some embodiments of the computer-implemented method, the method further comprises outputting indicia of the actual subterranean depths corresponding to respective zones within the core sample.

In some embodiments of the computer-implemented method, the correlating accounts for a compaction of the core sample tube as the core sampling tube is passed into the ground and the core sample enters the core sampling tube.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

In order that the invention may be better understood, exemplary embodiments will now be described by way of example only, with references to the accompanying drawings, wherein:

FIG. 3 is a perspective view of the device of FIG. 1 showing the motor, first and second distance measuring devices, the core sampling tube and the core sampler puck in an exemplary arrangement;

FIGS. 4A to 4C are sequential schematic side views of the device of FIG. 1 with the lower end of the core sampling tube entering the ground and a core sample entering the core sampling tube;

FIG. 5 is a schematic side of the device of FIG. 1 showing the first and second distance measuring devices in communication with the processing unit; and FIG. 6 is an exemplary view of outputted indicia from the processing unit.

DETAILED DESCRIPTION

With reference to the disclosure herein and the appended figures, a device and method for correlating core sample zones with an actual subterranean depth in accordance with various embodiments of the invention is provided.

Figure 1:
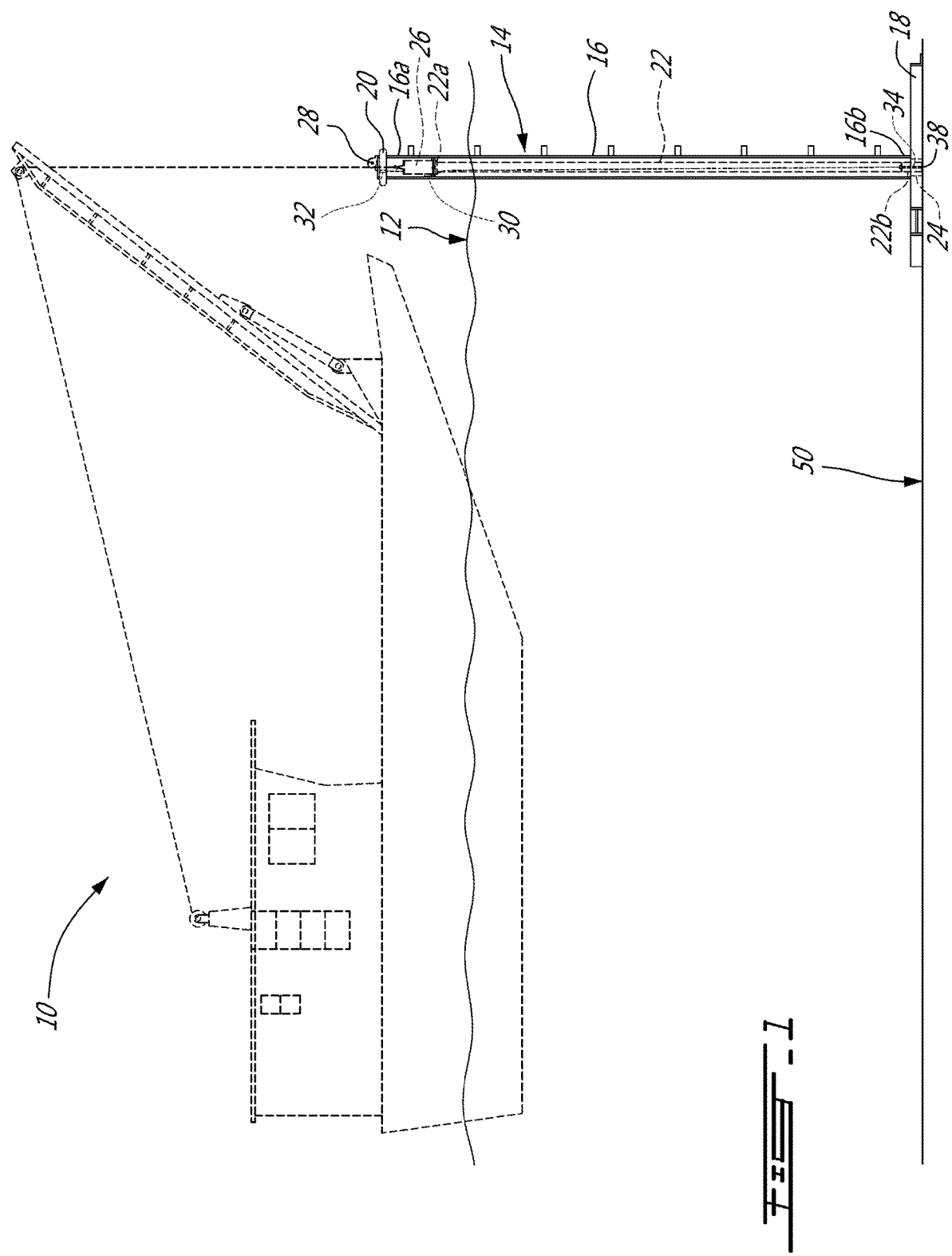
FIG. 1 is a schematic side view of an exemplary embodiment of the device for correlating core sample zones with an actual subterranean depth where the device is mounted on a boat.

With reference to FIG. 1, a generalized environment for use of the device 14 for correlating core sample zones with an actual subterranean depth of the instant subject matter is shown. Although shown for illustrative purposes with the device 14 coupled to a boat 10 (shown in ghost) floating on water 12, the device 14 may, in certain applications, be free-standing, coupled or operably mounted to a crane, a barge, a truck, a tracked-vehicle or a static structure in contemplated embodiments. The device comprises a rig frame 16 having a rig foot 18 operably coupled to near a rig frame lower end 16b and a component mounting surface 20 operably coupled to near a rig frame upper end 16a. The rig foot 18 has rig foot aperture 24, or other suitable opening, located therein for allowing a core sampling tube 22 to depend therethrough as lowered during use via a core sampling tube lowerer 28. The core sampling tube 22 has a core sampling tube lower end 22b and a core sampling tube upper end 22a. In some embodiments, the core sampling tube lower end 22b may be equipped with or have integrally formed thereon a cutter tip 38 to facilitate entry to the ground 50 or seabed 50, as shown in FIG. 1.

Located at or near the core sampling tube upper end 22a is a motor 26 operably coupled thereto. The motor 26 is provided for importing forces on the core sampling tube 22 such that the core sampling tube lower end 22b may enter the ground 50 as it is lowered via the core sampling tube lowerer 28. As shown in the figures, and specifically with reference to FIGS. 1 to 3, the core sampling tube lowerer 28, in preferred embodiments, may be provided as a winch 28 having an operable winch line 40 for controlling the descent of the core sampling tube 22 into the ground 50 as well as for removing the core sampling tube 22 from the ground after coring is complete. In other embodiments, the core sampling tube lowerer 28, although not shown in the figures, may be provided as hydraulic or pneumatic ram for controlling the descent of the core sampling tube 22 into the ground 50 as well as for removing the core sampling tube 22 from the ground. Furthermore, although shown in the figures with the winch line 40 coupled to the motor 26 and the winch 28 being coupled to the component mounting surface 20, it is contemplated that other arrangements and components may be possible in various applications for controlling the descent of the core sampling tube 50 and extraction from the ground 50.

In some embodiments, the motor 26 is provided as a rotational motor for imparting rotational forces on the core sampling tube 22 to aid entry in to the ground. In preferred embodiments, the motor 26 is provided a vibratory motor which imparts vibratory forces on the core sampling tube 22 causing the ground 50 immediately around the core sampling lower end 22b, an in some embodiments the cutter tip 38, to fluidize thus aiding entry into the ground 50 and lowering to a desired depth shown in FIGS. 4B and 4C, for example. The desired depth that the core sampling tube 22 is lowered into the ground 50 corresponds to B' and B" as noted in the schematic representations of FIGS. 4B and 4C and may be termed as the drive depth.

Figure 2:
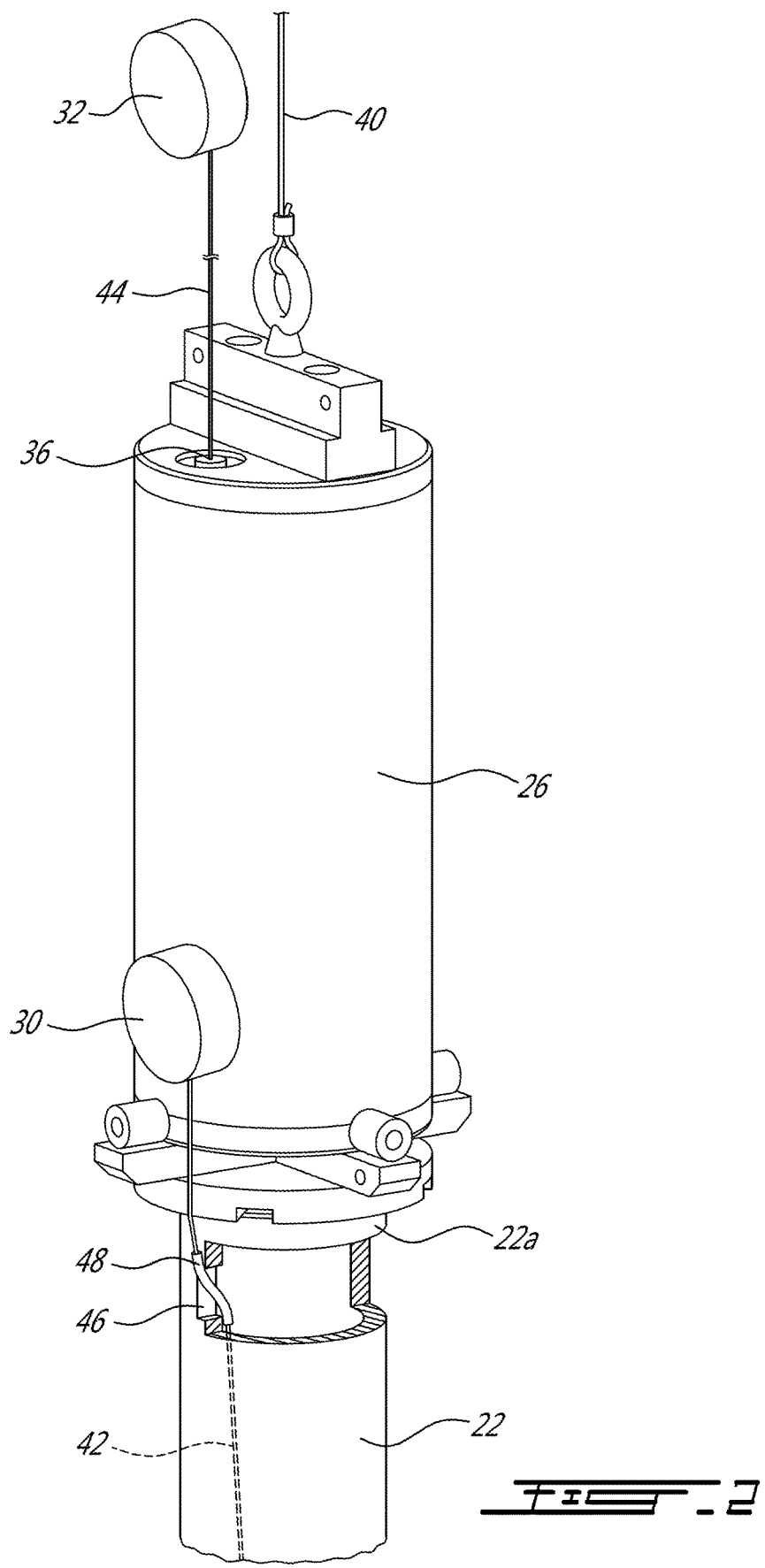
FIG. 2 is a perspective view of the device of FIG. 1 showing the motor, first and second distance measuring devices and a portion of the core sampling tube.
Figure 4A:
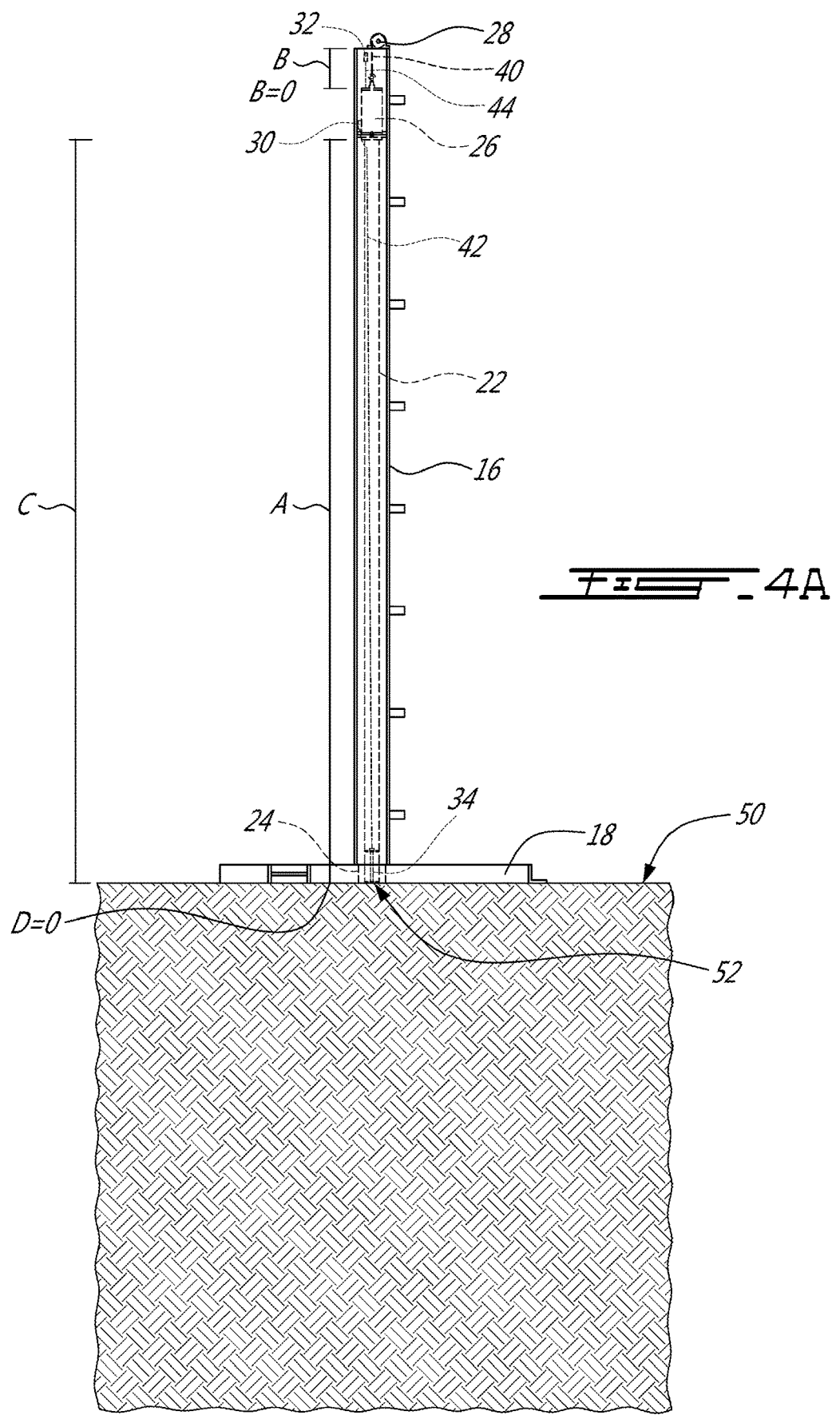

Turning now to FIG. 2, the motor 26, a portion of the core sampling tube 22 including the core sampling tube upper end 22a is shown devoid of the rig frame 16 for simplicity. There is provided a first distance measuring device 30 located near the core sampling tube upper end 22a, and in a preferred embodiment as shown in FIG. 2, coupled to the motor 26. Additionally, there is provided a second distance measuring device 32 located, as shown in FIG. 1, near the component mounting surface 20. The first distance measuring device 30 and second distance measuring device 32 are also shown FIG. 1 in a preferred arrangement of the device 14 for correlating core sample zones with an actual subterranean depth. The first distance measuring device 30 is provided for measuring a distance from the top of a core sample S entering the core sampling tube 22 and the core sampling tube upper end 22a, as shown schematically in FIGS. 4A to 4C, for example and corresponding to distances A, A' and A", respectively. It should be noted that as the core sampling tube 22 enters the ground 50 and the core sample S enters the hollow of the core sampling tube 22, the distances A, A' and A" are progressively shortened. The second distance measuring device 32, is provided for measuring the distance between the component mounting surface 20 and the core sampling tube upper; distance B, B' and B" as shown in FIGS. 4 to 4C, respectively, which also termed herein as the drive depth. Similar to the discussion above with respect first distance measuring device 30, as the core sampling tube 22 enters the ground, distances B, B', B" are progressively lengthened and provide the drive depth of the actual distance that the core sampling tube lower end 22b has entered the ground during operation.

With reference to FIG. 3, a core sampler puck 34 is provide and located within the hollow of the core sampling tube 22. The core sampler puck 34 is maintained within the hollow of the core sampling tube 22 and allowed to travel along the length of the sampling tube therein. Now, with reference to FIG. 4A, during operation, prior to the core sampling tube lower end 22b being inserted into the ground 50, the core sampler puck 34 is located under gravity near the core sampling tube lower end 22b and allowed to rest on top of the ground within the core sampling tube 22 at, in the case of a subsea application, the water-sediment interface 52, or in the case of a terrestrial-based application, the air-ground interface. Therefore, in an initial, pre-coring position as shown schematically in FIG. 4A, the core sample S length denoted as D equals zero. As the core sampling tube lower end 22b enters the ground 50 so as to take a core sample S, as shown in the sequential FIG. 4B, distance D increases, noted as D', and as shown in FIG. 4C when the core sampling tube lower end 22b is further lowered into the ground 50, denoted as D". Accordingly, as the core sampling tube lower end 22b is progressively lowered into the ground 50, distances A, A', and A" are shortened and distances B, B', B", D, D' and D" are lengthened where the first distance measuring device 30 measures the distances denoted by the A series and the second distance measuring device 32 measures the distance denoted by the B series as shown schematically in FIGS. 4A to 4C.

Both the first and second distance measuring devices 30 and 32 may be provided in various embodiments as laser measuring devices, radio frequency measuring devices, infrared measuring devices and string potentiometer measuring devices. Furthermore, each of the first and second distance measuring devices 30 and 32 may be calibrated to measure distances between two desired reference points as determined for various applications and embodiments. For example, the second distance measuring device 32 may be calibrated to take distance measurements between its location, shown in the figures as being located near the component mounting surface 20 and an external point 36 located on the motor 26. The first distance measuring device 30 shown in the figures as being mounted on the motor 26, may be calibrated to take distance measurements between a point, such as the core sampling tube upper end 22a and the top of the core sampler puck 34. However, it is contemplated that the various points may differ in various applications. For example, in some embodiments, the external point 36 may be located on or in the core sampling tube upper end 22a (not shown) and the first distance measuring device 30 may be located within the core sampling tube 22 and calibrated to measure from a top side of the core sampler puck 34 factoring in the size of the core sampler puck 34. Accordingly, the various measurement points would be calibrated into the system so as to obtain accurate measurements of A, A', A", B, B' and B", as required due to various chosen first and second distance measuring device mounting points and corresponding distance measuring points.

In various applications, the first and second distance measuring devices 30 and 32 may be provided as similar or identical device in that they both may be provided as laser measuring devices, radio frequency measuring devices, infrared measuring devices and string potentiometer measuring devices or in some embodiments, may differ from one another. For example, although not shown, it is contemplated that the first distance measuring device may be provided as string potentiometer measurement device whereas the second distance measuring device may be provided a laser measuring device. Such design options may be chosen as preferred based on the environment in which the device 14 is to be used. Taking a terrestrial-based application, the second distance measuring device 32 may be provided as a laser measuring device as air has a low refraction index and the first distance measuring device 30 may be provided as a string potentiometer measuring device since light reflection and refraction, in addition to debris with the hollow of the core sampling tube 22 may be problematic for laser or other optical measuring devices. In subsea applications, where both the first and second distance measuring devices 30 and 32 may be wholly or partially submersed under water, having both the first and second distance measuring devices 30 and 32 provided as string potentiometer measuring devices may be desirable to provide more accurate measurements in a given medium.

In preferred embodiments, both the first and second distance measuring devices 30 and 32 are provided as string potentiometer measuring devices where the first distance measuring device 30 has a first string potentiometer line 42 dependable therefrom and coupled to the core sampler puck 34 and the second distance measuring device 32 has a second string potentiometer line 44 dependable therefrom and coupled to the external point, as shown in the figures. With reference to FIG. 2 the first string potentiometer line 42 depends through a core sampling tube aperture 46. In some embodiments, as that shown in FIG. 2, is guided though the core sampling tube aperture 46 via a line guide 48 to allow smooth extension and retraction of the first string potentiometer line 42 through the core sampling tube aperture 46 and to inhibit chaffing.

Briefly, string potentiometer measurement systems or cable-actuated position sensors generally comprise a measuring cable or line 42/44, a spool (not shown), a torsion spring (not shown), and a rotational sensor (not shown). In some applications, the rotational sensor is fitted a transducer which is capable of transmitting electronic information received from the rotational sensor to another device for analysis and/or processing which can then be interpreted by an operator. The line 42/44 is generally maintained under tension by the torsion spring, or other tension creating means, acting on the spool around which a portion of the line 42/44 is wrapped. The torsion spring, in general is set to bias the line in a retracted state (or maintained state which can be urged to retract as in the case of line 44, in some embodiments) such than when an extending force acting on the line 42/44 is relieved from the line, the spool biasingly retracts the line. The spool, being connected to a shaft, is allowed to rotate under tension. The rotation of the spool as the line 42/44 is extended or retracted is measured by the rotational sensor and converted to a distance corresponding to the distance the line 42/44 is extended or retracted.

As noted above, an operator does not know for certain whether sediment, or in other words, a core sample S is entering the core sampling tube 22 as it enters the ground 50. Furthermore, as a core sample S enters the core sampling tube 22 it may be compressed in certain zones based on the sediment layers through which it has penetrated. Therefore, when the core sample S is extracted for analysis the revealed subterranean depth of a given zone in the core sample S may not correspond to the true subterranean depth. The device and method disclosed herein allows an operator to receive feedback as to whether a core sample S is entering the core sampling tube 22, and also to be able to correlate an actual subterranean depth (the drive depth) denoted in FIGS. 4A to 4C as B, B' and B", with a given zone of a core sample S. For example, shown in FIG. 6 for illustration purposes, the drive depth, B, B' and B" is outputted as indicia 58 which may be provided to the operator in a chart format and the length of the sample entering the hollow of the core sampling tube 22 is provided to the operator as D, D' and D". Distance E, schematically shown in FIG. 4C is the amount of sample compaction at a given depth and can also be provided to the operator in the indicia 58 as shown in FIG. 6. Distance C as shown in FIG. 4A to 4C is a constant distance, or length of the core sampling tube 22. Distances A, A' and A" decrease as a core sample S enters the hollow of the core sampling tube 22 and distance D, D' and D" increase where distance D, D' and D" corresponds to the length of the core sample S which has entered the hollow of the core sampling tube at a given depth.

Turning now to FIG. 4A specifically where an embodiment of the device is shown ready to take a core sample in an initial position with the core sampling tube lower end 22b and the core sampler puck 34 resting on the ground at the water-sediment interface or ground-air interface 52, distances B and D are calibrated to zero and distance A is set to the length of the core sampling tube penetrable into the ground 50. Accordingly, distance C is equal to the sum of distances A and D. And, as the core sampling tube 22 enters the ground 50 and a core sample S is taken, should there be any compaction of the core sample S, distance C is equal to distances A, D and E. Bearing this in mind, distance E, the amount of core sample compaction can be expressed by the following equation for any given core sampling tube 22 drive depth B:

$$E = C - (A+B) \qquad \text{Equation 1.}$$

Similarly, the length of the core sample S within the hollow of the core sampling tube 22 for any given core sampling tube drive depth can be expressed as:

$$D = C - A \qquad \text{Equation 2.}$$

For example, if distance B and distance D are equal operator knows that the core sample S is entering the core sampling tube 22 with no compression or compaction. If distance B does not equal distance D, then an operator will know that there is a degree of compression or compaction of the core sample S and correlation as to the actual subterranean depth and a given core sample zone must be made, factoring in distance E in order to determine the actual subterranean depth from where a given zone of the core sample S was taken.

Turning now to FIG. 5, in embodiments equipped with a processing unit 54, the processing unit 54 receives distance information from the first distance measuring device 30 via data input/transmission means 56a and from the second distance measuring device 32 via data input/transmission means 56b. The respective data inputs/transmission means 56a and 56b may be fed to the processing unit 54 by direct cable link, radio frequency link, infrared link or other modes of data transmission as may be known in the art and suitable for a given application and operating of the device 14. In some embodiments, the processing unit 54 may include a non-transitory computer-readable medium having statements and instructions for implementation of the above-discussed calculations so as to provide information for correlating a given core sample zone with an actual subterranean depth. For example, such information can be provided to the operator as the indicia 58 shown in FIG. 6 in a chart format. Additionally, as also shown FIG. 6, a graphical representation 60a/60b of the core sample compression 60a correlation between the actual subterranean depth 60b (drive depth B, B' B") corresponding to a given core sample zone may be provided to the operator in a distance-skewed line format where the compression factor E of the core sample S is taken into account. Such information may be provided as print-out or on a display screen, indicia 58. Accordingly, in some embodiments the processing unit 54 is therefore configured to provide 'real time' feedback on core sampling performance to an operator.

In some embodiments, the calculated compression factor E may be provided to the operator as a cumulative compression E amount taking into account the total compression of the core sample S over the course of the core sampling process and/or it may be provided to the operator as the amount of compression per unit of drive depth or in other word the incremental compression E', as shown in FIG. 6. In preferred embodiments, both the cumulative compression amount E of the core sample S and the amount of incremental compression E' is provided to the operator.

In terms of measuring the respective distances noted above, such measurements may be taken in any number units. However, the units are generally measured centimeters or meters or a combination thereof, as schematically shown in FIG. 6, and accuracies in the order of less than 1.0 cm are rendered when a given core sample S is correlated with any actual subterranean depth.

In conjunction with the instantly disclosed device 14 there is also provided a method for correlating a core sample S with an actual subterranean depth. For example, through the use of the device 14, an operator is provided with indicia 58 as to an actual subterranean depth from where a given core sample zone has been taken. Once the core sample S is extracted from the ground 50, various points along a core sample S can be correlated with an actual subterranean distance, for example, utilizing the information or indicia 58 provided as schematically shown in FIG. 6. Such information may take the form where distances measured on an extracted core sample are scaled-up to life-size measurements from the sample taken indicia shown at 60a and correlated to the core depth shown at 60b of FIG. 6.

It is to be understood that the above description it is intended to be illustrative, and not restrictive. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific exemplary embodiments, it will be evident that various modifications and changes may be made to these embodiments without departing from the broader spirit and scope of the disclosed subject matter as defined by the appended claims.

What is claimed is:

1. A non-transitory computer-readable medium comprising computer-executable instructions for correlating core sample zones in a core sample taken using a core sampling tube, with an actual subterranean depth, by:
    measuring, via a first measuring device, a decreasing distance between a core sampler puck maintained within and movable along an internal length of the core sampling tube, and an upper end of the core sampling tube;
    measuring, via a second measuring device, an increasing distance to the upper end of the core sampling tube as the core sampling tube is passed into the ground and the core sample enters the core sampling tube; and
    correlating said decreasing distance and said increasing distance so as to render the actual subterranean depth corresponding to a given core sample zone within the core sample.

2. The non-transitory computer-readable medium as defined in claim 1, further comprising instructions to output a chart rendering the actual subterranean depth corresponding to said given zone within the core sample.

3. The non-transitory computer-readable medium as defined in claim 1, further comprising instructions to output a graphical representation of the actual subterranean depth corresponding to said given zone within the core sample.

4. The non-transitory computer-readable medium as defined in claim 1, further comprising instructions to output indicia of the actual subterranean depths corresponding to respective zones within the core sample.

5. The non-transitory computer-readable medium as defined in claim 1, wherein said correlating accounts for a compaction of the core sample tube as the core sampling tube is passed into the ground and the core sample enters the core sampling tube.

6. A computer-implemented method, to be implemented by a processing unit, for correlating core sample zones in a core sample taken using a core sampling tube, with an actual subterranean depth, comprising:
- measuring, via a first measuring device, a decreasing distance between a core sampler puck maintained within and movable along an internal length of the core sampling tube, and an upper end of the core sampling tube;
- measuring, via a second measuring device, an increasing distance to the upper end of the core sampling tube as the core sampling tube is passed into the ground and the core sample enters the core sampling tube; and
- correlating said decreasing distance and said increasing distance so as to render the actual subterranean depth corresponding to a given core sample zone within the core sample.

7. The computer-implemented method as defined in claim 6, further comprising rendering the actual subterranean depth corresponding to said given zone within the core sample in a chart.

8. The computer-implemented method as defined in claim 6, further comprising outputting a graphical representation of the actual subterranean depth corresponding to said given zone within the core sample.

9. The computer-implemented method as defined in claim 6, further comprising outputting indicia of the actual subterranean depths corresponding to respective zones within the core sample.

10. The computer-implemented method as defined in claim 6, wherein said correlating accounts for a compaction of the core sample tube as the core sampling tube is passed into the ground and the core sample enters the core sampling tube.

* * * * *